(12) United States Patent
Anand

(10) Patent No.: US 10,813,624 B2
(45) Date of Patent: Oct. 27, 2020

(54) ULTRASOUND DISPLAY METHOD

(71) Applicant: Carestream Health, Inc., Rochester, NY (US)

(72) Inventor: Ajay Anand, Rochester, NY (US)

(73) Assignee: Carestream Health, Inc., Rochester, NY (US)

( * ) Notice: Subject to any disclaimer, the term of this patent is extended or adjusted under 35 U.S.C. 154(b) by 988 days.

(21) Appl. No.: 15/164,935

(22) Filed: May 26, 2016

(65) Prior Publication Data

US 2017/0119352 A1 May 4, 2017

Related U.S. Application Data

(60) Provisional application No. 62/248,528, filed on Oct. 30, 2015.

(51) Int. Cl.
| | | |
|---|---|---|
| *A61B 8/00* | (2006.01) | |
| *A61B 8/08* | (2006.01) | |
| *G06T 7/11* | (2017.01) | |
| *A61B 8/06* | (2006.01) | |
| *G06T 7/00* | (2017.01) | |

(52) U.S. Cl.
CPC ............ *A61B 8/463* (2013.01); *A61B 8/0866* (2013.01); *A61B 8/0891* (2013.01); *A61B 8/4405* (2013.01); *A61B 8/465* (2013.01); *A61B 8/469* (2013.01); *A61B 8/486* (2013.01); *A61B 8/488* (2013.01); *A61B 8/523* (2013.01); *A61B 8/5207* (2013.01); *A61B 8/5215* (2013.01); *A61B 8/54* (2013.01); *G06T 7/11* (2017.01); *A61B 8/06* (2013.01); *G06T 7/0012* (2013.01); *G06T 2207/10024* (2013.01); *G06T 2207/10132* (2013.01); *G06T 2207/30024* (2013.01); *G06T 2207/30101* (2013.01)

(58) Field of Classification Search
CPC ..... A61B 8/463; A61B 8/0866; A61B 8/0891; A61B 8/4405; A61B 8/465; A61B 8/469; A61B 8/486; A61B 8/488; A61B 8/5207; A61B 8/5215; A61B 8/523; A61B 8/54; A61B 8/06; G06T 7/11; G06T 7/0012; G06T 2207/10024; G06T 2207/10132; G06T 2207/30024; G06T 2207/30101
See application file for complete search history.

(56) References Cited

U.S. PATENT DOCUMENTS

| | | |
|---|---|---|
| 5,370,120 A | 12/1994 | Oppelt et al. |
| 6,705,995 B1 | 3/2004 | Poland et al. |
| 8,285,357 B2 | 10/2012 | Gardner et al. |

(Continued)

OTHER PUBLICATIONS

Thomas L. Szabo, PhD et al., Ultrasound Transducer Selection in Clinical Imaging Practice, American Institute of Ultrasound in Medicine, J Ultrasound Med 2013, vol. 32, pp. 573-582.

(Continued)

*Primary Examiner* — Carolyn A Pehlke

(57) ABSTRACT

A method displays, in response to a user selection of a first viewing mode, an ultrasound image in grayscale and determines a region of interest within the displayed grayscale ultrasound image. In response to an operator instruction to switch to a second viewing mode that is different from the first viewing mode, a modified ultrasound image is generated comprising the region of interest. The method displays the modified ultrasound image including the region of interest, wherein one or more portions of the modified image are highlighted.

4 Claims, 7 Drawing Sheets

(56) References Cited

U.S. PATENT DOCUMENTS

| | | |
|---|---|---|
| 2006/0098853 A1 | 5/2006 | Roundhill et al. |
| 2007/0239001 A1 | 10/2007 | Mehi et al. |
| 2010/0130866 A1 | 5/2010 | Main et al. |
| 2010/0305440 A1 | 12/2010 | Lee et al. |
| 2014/0059486 A1 | 2/2014 | Sasaki et al. |
| 2014/0221838 A1 | 8/2014 | Loupas et al. |

OTHER PUBLICATIONS

International Search Report, International application No. PCT/US2016/053228, dated Dec. 2016, 2 pages.

ULTRASOUND DISPLAY METHOD

CROSS REFERENCE TO RELATED APPLICATIONS

This application claims the benefit of U.S. Provisional application U.S. Ser. No. 62/248,528, provisionally filed on Oct. 30, 2015, entitled "ULTRASOUND DISPLAY METHOD", in the name of Ajay Anand, incorporated herein by reference in its entirety.

TECHNICAL FIELD

The invention relates generally to the field of medical ultrasound systems and methods, and in particular to a method for improved workflow for ultrasound apparatus operation.

BACKGROUND

Ultrasound imaging systems/methods are known, such as those described, for example, in U.S. Pat. No. 6,705,995 (Poland), U.S. Pat. No. 5,370,120 (Oppelt), and U.S. Pat. No. 8,285,357 (Gardner), all of which are incorporated herein in their entirety. Various applications for diagnostic ultrasound systems are given, for example, in the article entitled "Ultrasound Transducer Selection In Clinical Imaging Practice", by Szabo and Lewin, *Journal of Ultrasound Medicine*, 2013; 32:573-582, incorporated herein by reference in its entirety.

Ultrasound utilizes sound waves at frequencies higher than those perceptible to the human ear. Ultrasonic images known as sonograms are generated as a result of pulsed ultrasonic energy that has been directed into tissue using a probe. The probe obtains echoed sound energy from the internal tissue and provides signal content that represents the different sound reflectivity exhibited by different tissue types. This signal content is then used to form images that visualize features of the internal tissue. Medical ultrasound, also known as diagnostic sonography or ultrasonography, is used as a diagnostic imaging technique used to help visualize features and operation of tendons, muscles, joints, vessels and internal organs of a patient.

FIGS. 1A-1B and FIGS. 2-3 show exemplary portable ultrasound systems 10 that use a cart/base/support, cart 12, a display/monitor 14, one or more input interface devices 16 (such as keyboard or mouse), and a generator 18. The display/monitor 14 can also be a touchscreen to function as an input device. As illustrated, the ultrasound system 10 can be a mobile or portable system designed to be wheeled from one location to another. As FIG. 2 shows, the ultrasound system 10 has a central processing unit CPU 20 that provides control signals and processing capabilities. CPU 20 is in signal communication with display 14 and interface device 16, as well as with a storage device 22 and an optional printer 24. A transducer probe 26 provides the ultrasound acoustic signal and generates an electronic feedback signal indicative of tissue characteristics from the echoed sound.

FIG. 3 shows an example of an ultrasound system 10 in use with an image provided on display/monitor 14.

Different types of images, with different appearance, can be formed using sonographic apparatus. The familiar monochrome B-mode image displays the acoustic impedance of a two-dimensional cross-section of tissue. Other types of image can use color or other types of highlighting to display specialized information such as blood flow, motion of tissue over time, the location of blood, the presence of specific molecules, tissue stiffness, or the anatomy of a three-dimensional region.

Accordingly, the ultrasound systems of FIGS. 1A-3 are typically configured to operate within at least two different ultrasound modes. As such, the system provides means to switch between the at least two different ultrasound modes. Such a multi-mode configuration, along with techniques for switching between modes, are known to those skilled in ultrasound technology.

In conventional workflow, the sonographer or other operating practitioner begins an examination with B-mode imaging in order to locate the anatomy or region of interest (ROI). Then, once the ROI is located, the sonographer switches to a suitable imaging mode for the particular requirements of an exam. In switching from one mode to the next, however, the sonographer must often readjust various equipment settings and may need to manually identify or adjust the ROI for the new mode. The need for this type tedious and repeated adjustment complicates sonographer workflow, adding time and steps to the procedure to obtain the desired image.

Accordingly, there is a desire to provide improved workflow for the sonographer and to address problems that can result from changing ultrasound equipment mode.

SUMMARY

Certain embodiments described herein address the need for improved workflow for operating ultrasound apparatus. Embodiments of the present disclosure enable the operator to change operating modes with reduced steps to adjust parameters for imaging in different modes.

According to at least one aspect of the invention, there is described a method comprising: displaying, in response to a user selection of a first viewing mode, an ultrasound image in grayscale; determining a region of interest within the displayed grayscale ultrasound image; in response to an operator instruction to switch to a second viewing mode that is different from the first viewing mode, generating a modified ultrasound image comprising the region of interest; and displaying the modified ultrasound image including the region of interest, wherein one or more portions of the modified image are highlighted.

These aspects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

DETAILED DESCRIPTION OF THE EMBODIMENTS

Figure 1B:
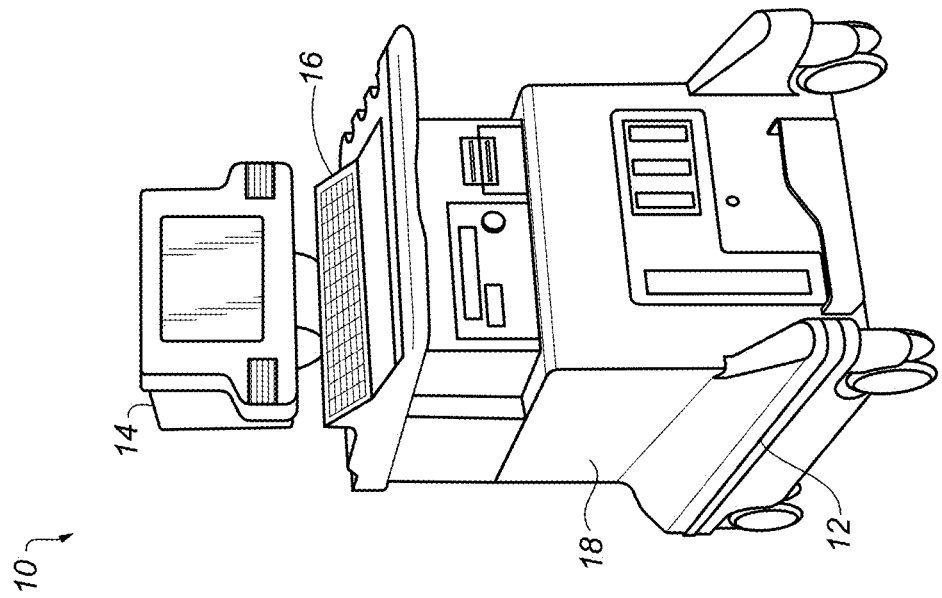
FIGS. 1A and 1B show exemplary ultrasound systems.

The following is a detailed description of embodiments of the invention, reference being made to the drawings in which the same reference numerals identify the same elements of structure in each of the several figures.

Where they are used in the context of the present disclosure, the terms "first", "second", and so on, do not necessarily denote any ordinal, sequential, or priority relation, but are simply used to more clearly distinguish one step, element, or set of elements from another, unless specified otherwise.

As used herein, the term "energizable" relates to a device or set of components that perform an indicated function upon receiving power and, optionally, upon receiving an enabling signal.

In the context of the present disclosure, the phrase "in signal communication" indicates that two or more devices and/or components are capable of communicating with each other via signals that travel over some type of signal path. Signal communication may be wired or wireless. The signals may be communication, power, data, or energy signals. The signal paths may include physical, electrical, magnetic, electromagnetic, optical, wired, and/or wireless connections between the first device and/or component and second device and/or component. The signal paths may also include additional devices and/or components between the first device and/or component and second device and/or component.

In the context of the present disclosure, the term "subject" is used to describe the patient that is undergoing ultrasound imaging. The terms "sonographer", "technician", "viewer", "operator", and "practitioner" are used to indicate the person who actively operates the sonography equipment.

The term "highlighting" for a displayed element or feature has its conventional meaning as is understood to those skilled in the information and image display arts. In general, highlighting uses some form of localized display enhancement to attract the attention of the viewer. Highlighting a portion of a display, such as a particular value, graph, message, or other element can be achieved in any of a number of ways, including, but not limited to, annotating, displaying a nearby or overlaying symbol, outlining or tracing, display in a different color or at a markedly different intensity or grayscale value than other image or information content, blinking or animation of a portion of a display, or display at larger scale, higher sharpness, or contrast.

General Information about an Ultrasound System.

Figure 1A:
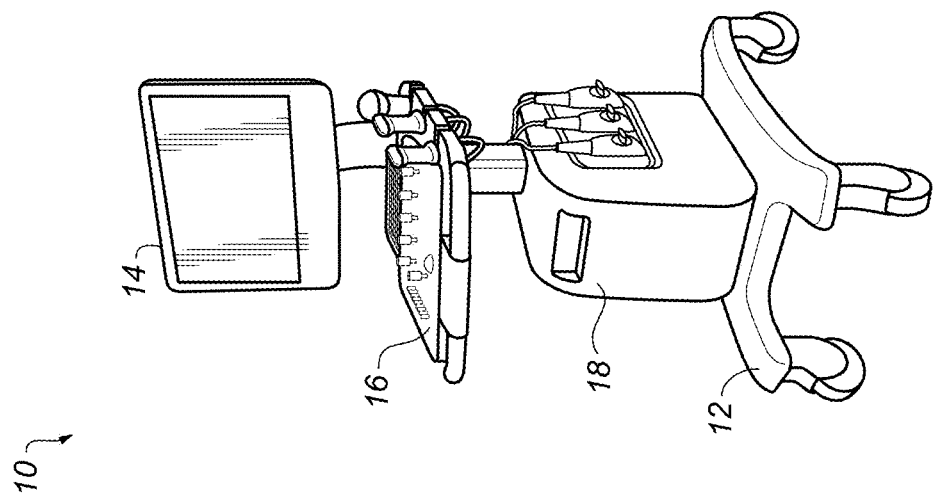
Figure 2:
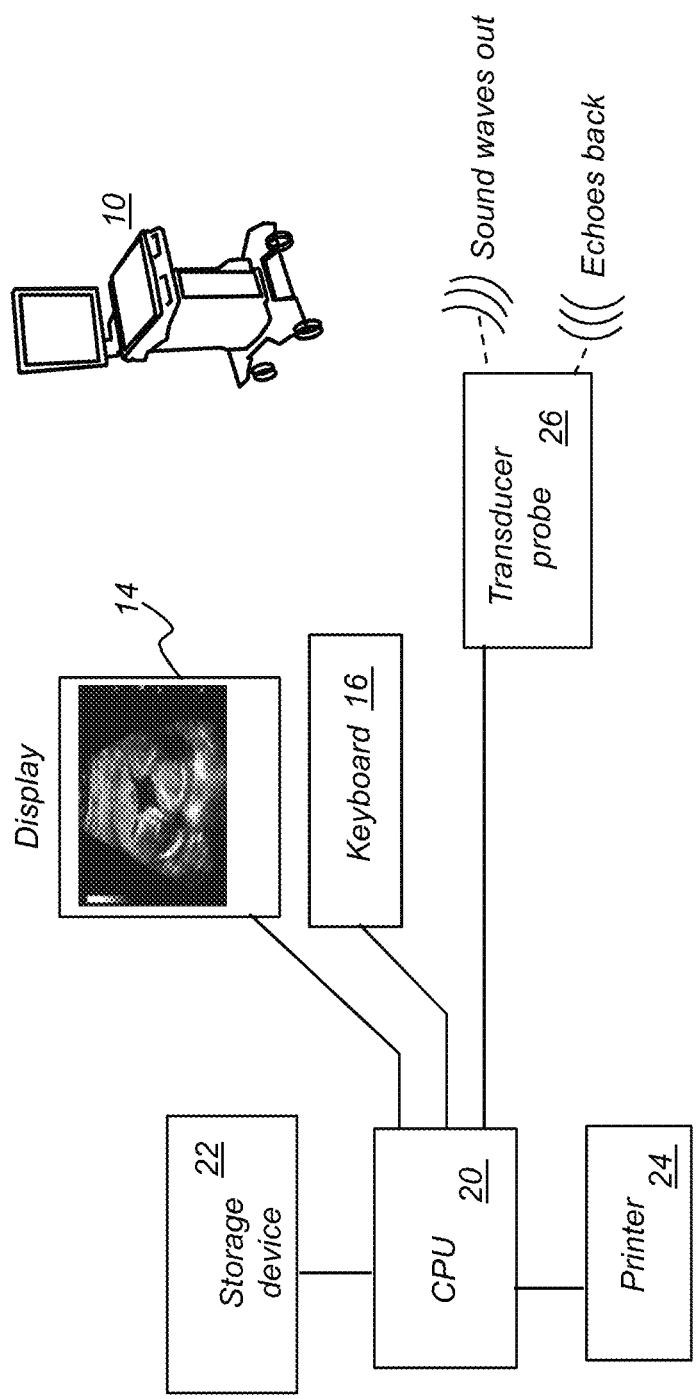
FIG. 2 shows a schematic of an exemplary ultrasound system.
Figure 3:
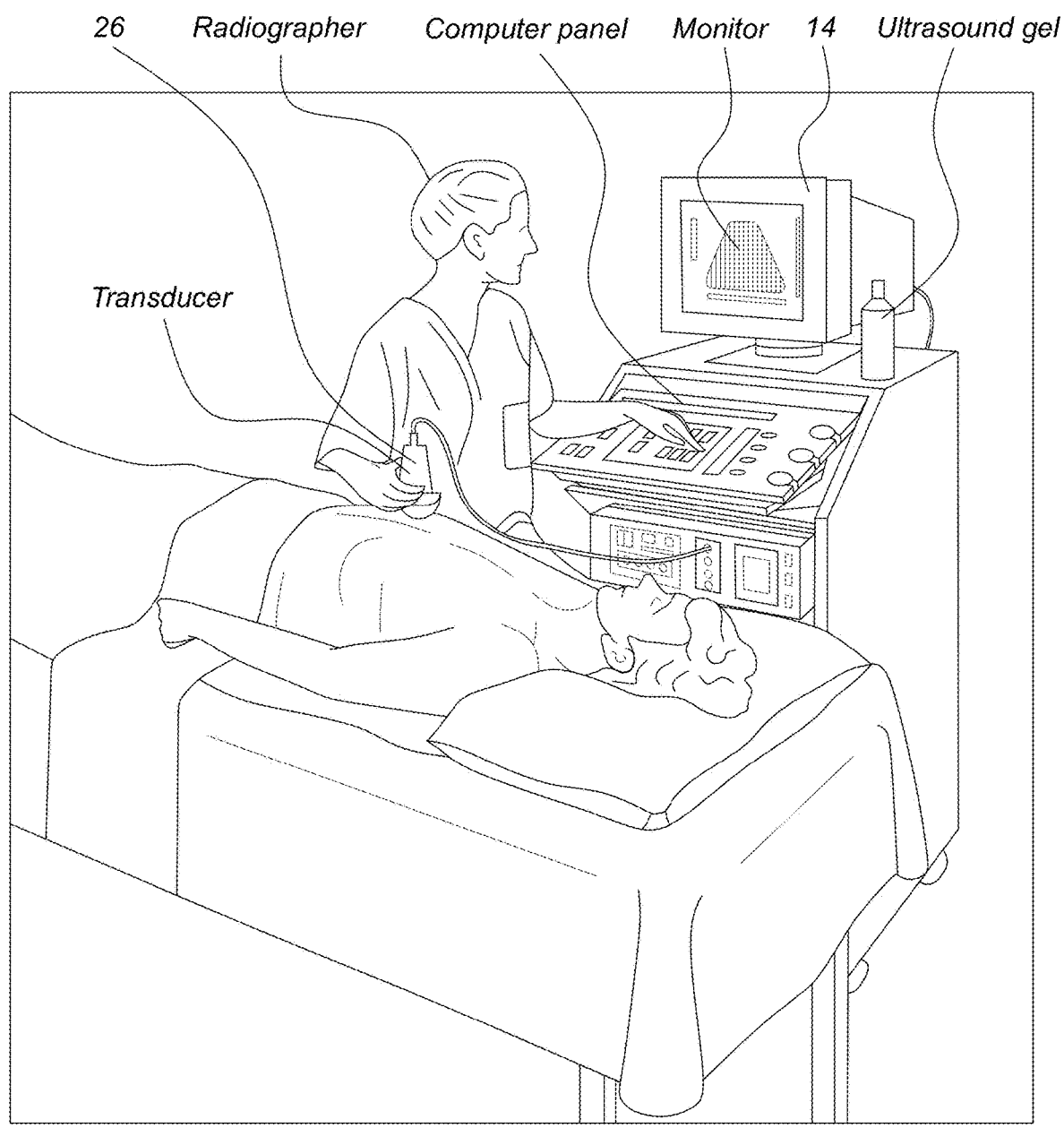
FIG. 3 illustrates a sonographer using an exemplary ultrasound system.

The ultrasound system, shown by way of example in FIGS. 1A and 1B, can include image processing system, a user interface and a display. The image processing system includes a memory and a processor. Additional, different or fewer components may be provided in the system or image processing system. In one embodiment, the system is a medical diagnostic ultrasound imaging system. The memory is a RAM, ROM, hard drive, removable media, compact disc, DVD, floppy disc, tape, cache memory, buffer, capacitor, combinations thereof or any other now known or later developed analog or digital device for storing information. The memory is operable to store data identifying a selected point for identifying a region of interest. The memory is operable to store data identifying one or a plurality of region of interest. Information from the user interface indicating a position on an image on the display is used to determine a spatial relationship of a user selected point to a scanned region or image position. The selected point is an individual or single point in one embodiment that may be a point selected within a line, area or volume. Additional or different information may be also stored within the memory. The processor is general processor, application specific integrated circuit, digital signal processor, controller, field programmable gate array, digital device, analog device, transistors, combinations thereof or other now known or later developed devices for receiving analog or digital data and outputting altered or calculated data. The user input is a track ball, mouse, joy stick, touch pad, buttons, slider, knobs, position sensor, combinations thereof or other now known or later developed input devices. The user input is operable to receive a selected point from a user. For example, the user positions a cursor on an image displayed on the display. The user then selects a position of the cursor as indicating a point for a region of interest. The display is a CRT, LCD, plasma screen, projector, combinations thereof or other now known or later developed devices for displaying an image, a region of interest, region of interest information and/or user input information.

Ultrasound Imaging Modes

Modes of ultrasound used in medical imaging include the following:

A-mode: A-mode (amplitude mode) is the simplest type of ultrasound. A single transducer scans a line through the body with the echoes plotted on screen as a function of depth. Therapeutic ultrasound aimed at a specific tumor or calculus is also A-mode, to allow for pinpoint accurate focus of the destructive wave energy.

B-mode or 2D mode: In B-mode (brightness mode) ultrasound, a linear array of transducers simultaneously scans a plane through the body that can be viewed as a two-dimensional image on screen. Sometimes referred to as 2D mode, this mode is generally the starting point for exam types that use other modes.

C-mode: A C-mode image is formed in a plane normal to a B-mode image. A gate that selects data from a specific depth from an A-mode line is used; then the transducer is moved in the 2D plane to sample the entire region at this fixed depth. When the transducer traverses the area in a spiral, an area of 100 $cm^2$ can be scanned in around 10 seconds.

M-mode: In M-mode (motion mode) ultrasound, pulses are emitted in quick succession. With each pulse, either an A-mode or B-mode image is acquired. Over time, M-mode imaging is analogous to recording a video in ultrasound. As the organ boundaries that produce reflections move relative to the probe, this mode can be used to determine the velocity of specific organ structures.

Doppler mode: This mode makes use of the Doppler effect in measuring and visualizing blood flow.

Color Doppler: Velocity information is presented as a color-coded overlay on top of a B-mode image. This mode is sometimes referred to as Color Flow or color mode.

Continuous Doppler: Doppler information is sampled along a line through the body, and all velocities detected at each point in time are presented (on a time line).

Pulsed wave (PW) Doppler: Doppler information is sampled from only a small sample volume (defined in 2D image), and presented on a timeline.

Duplex: a common name for the simultaneous presentation of 2D and (usually) PW Doppler information. (Using modern ultrasound machines, color Doppler is almost always also used; hence the alternative name Triplex.).

Pulse inversion mode: In this mode, two successive pulses with opposite sign are emitted and then subtracted from each other. This implies that any linearly responding constituent will disappear while gases with non-linear compressibility stand out. Pulse inversion may also be used in a similar manner as in Harmonic mode.

Harmonic mode: In this mode a deep penetrating fundamental frequency is emitted into the body and a harmonic overtone is detected. With this method, noise and artifacts due to reverberation and aberration are greatly reduced. Some also believe that penetration depth can be gained with improved lateral resolution; however, this is not well documented.

While conducting an ultrasound exam, the sonographer may often switch between multiple ultrasound modes. For example, the sonographer first operates in a B-mode in order to coarsely locate the ROI. The sonographer then transitions to a Doppler mode before moving back to the B-mode. For some particular examinations, there are pre-set (or pre-determined or pre-defined) steps/modes that the sonographer must follow. That is, the ordered sequence of modes used in a particular exam type can be predefined for the operator.

For carotid artery imaging, for example, the exam typically follows a progression of modes such as: (i) B-mode for initial positioning and establishing reference coordinates of the sample volume; (ii) Color Flow mode for improved visualization of blood vessels; and (iii) Pulse wave Doppler mode for highlighting blood flow within the sample volume.

For heart imaging, the exam progression can use B-mode or M-mode imaging for auto-positioning of the cursor, followed by Color Flow or pulse wave Doppler modes.

The Applicant has noted that in combination modes (such as Color Flow and Doppler), the sonographer preferably optimizes the settings for each of the modes individually. Also, based on the physical orientation of the anatomy on the displayed image, some of the settings are optimized on a per patient basis. This per patient optimization does not lend itself to global customization.

When viewing an ultrasound image on the display, the particular area of the displayed image that is of interest to the sonographer or other practitioner is referred to as the Region of Interest (ROI) or ROI extent. As the sonographer conducts the examination and switches between modes, the size and position, as well as the apparent shape of the ROI may change. This can require that the operator readjust settings in order to more accurately show features of anatomy in the ROI.

The region of interest (ROI) can be defined in any of a number of ways. In conventional practice, the ROI is defined by multiple points or vertices that define a shape, such as defining a rectangle or other parallelogram by its four corners, for example. Alternately, the ROI can be defined by a point and a distance, such as a center point and a radius or function of the distance from the point to a single boundary. The distance may be, for example, any of a radius, circumference, diagonal, length or width, diameter or other characteristic of a shape. The region of interest can alternately be defined by a point and two distances, such as a distance to each of two boundaries. In another arrangement, the region of interest can be a pre-defined shape positioned around a point, such as a square, rectangle, oval or combination thereof.

The sonography workflow typically begins with acquisition of a grayscale mode image acquisition and display (such as the B-mode image illustrated in FIG. 4) in order to survey the anatomy. Depending on the exam type, the operator then switches to a different imaging mode such as Color Doppler mode (sometimes referred to as Color Flow mode or Color mode) to evaluate a sub-region of the originally viewed grayscale image in order to obtain additional clinical information and further characteristics of the anatomy or tissue within a particular ROI. The ROI in a polychromatic or color imaging mode can be indicated by a rectangular, parallelogram, trapezoidal or another regularly shaped outline. In a typical ultrasound system, the spatial extent of the color ROI is a partial subset of the larger B-mode image; some portions of the B-mode image may not be displayed in the subsequent color mode. This is because the computational processing demands for polychromatic presentation are significantly higher than those for grayscale B-mode processing and rendering; this is among the tradeoffs commonly established in conventional practice.

Figure 5:
FIG. 5 shows a displayed ultrasound image having a region of interest, wherein a portion of the region of interest is highlighted in color.
Figure 4:
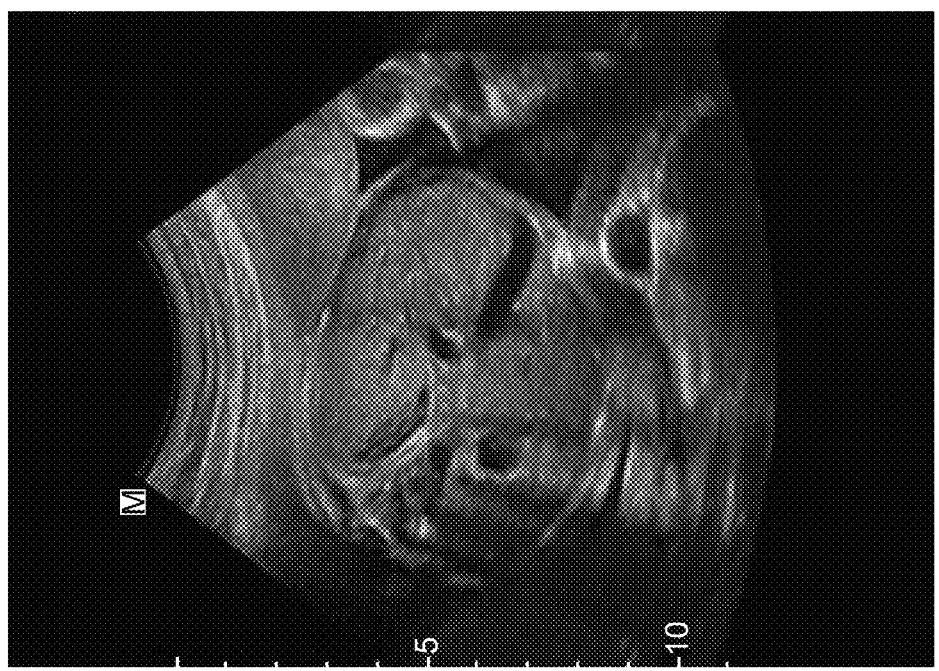
FIG. 4 shows a displayed ultrasound image having a region of interest, shown in grayscale.

By way of example, FIG. 4 shows B-mode ultrasound image, displayed as a grayscale image. FIG. 5 shows an image with the same ROI having color highlighting, obtained in Color Flow mode.

One difficulty for ultrasound workflow relates to changes in the field of view that can be inherent between modes. As noted earlier, switching between modes often requires that the sonographer manually determine where to define or place the ROI to obtain the information of interest. For example, the anatomy of interest may be a blood vessel, best viewed when highlighted in Color Flow mode. The sonographer initially locates the sample volume, in grayscale, in B-mode. Then, after switching to Color Flow or other polychromatic mode, the sonographer manually repositions the ROI to include the blood vessel. As this example illustrates, the displayed image (in the second, polychromatic mode) may differ from the original grayscale image in size, position, and centering, since the field of view often changes between modes.

With some systems, for example, the sample volume region (i.e., ROI) of the Color Flow mode display is typically smaller than the original B-mode region. The ROI is typically located at some default position that is pre-programmed in the system and may not be related to the location desired by the sonographer. When this type of situation occurs, as part of the workflow, the sonographer must execute additional tasks, and must enter more key strokes or instruction entries in order to position the ROI in the area of clinical interest.

Applicant has developed a method whereby the workflow requirements are improved/enhanced, for example, with fewer key strokes for adjusting between displayed views upon mode switching. In the Applicant's method, a set of standard workflows are defined, based on the types of imaging that are typically performed at a site and on the sequence of mode switches that typically occur. Processing logic for the ultrasound system is configured with prior knowledge of the set of standard workflows and is thus even able to anticipate (i.e., prepare in advance for) expected switching between modes according to the standard workflow that is specified for the patient and is currently being followed. Using this approach, when switching between a first and second/different mode, the ultrasound system attempts to maintain the sonographer's ROI from the prior or first mode, or, alternately, to re-position the ROI to a particular spatial location that is likely to be more clinically-useful based on the exam type during mode switching. When an ultrasound exam begins, the sonographer specifies or otherwise chooses the tissue preset (also known as exam type) or, in some instances, as an exam protocol from a pre-defined menu. This can provide the system with valuable a priori knowledge that indicates the most likely sequence of mode changes as the exam progresses.

With Applicant's method, there is displayed an ultrasound image on a display of an ultrasound system. The image is displayed in response to a viewer selection of a first viewing mode. The displayed image is initially in a mode that provides a grayscale image, such as the B-mode image in FIG. 4.

As the sonographer conducts the ultrasound examination, the ultrasound system, as a background process, determines the extent of the region of interest, also termed the ROI extent, within the displayed ultrasound image. This ROI extent determination preferably does not interpret or disturb the examination being conducted by the sonographer. The ROI extent determination is done by the system transmitting, receiving, and processing the signals suited for a different, anticipated mode of operation, and determining at which location the information for the new mode resides. Information to anticipate operating mode succession can be provided from stored data, such as from standard workflow mode sequences that have been pre-programmed or recorded by the ultrasound imaging apparatus. According to an alternate embodiment, the ultrasound imaging apparatus applies logic software to "learn" the sequence of commands and adjustments typically used and required for particular types of exams. This learned information can then be used to advance the system setup for anticipated operating mode changes.

Since standard ultrasound workflows are well-defined, the system can anticipate upcoming mode changes and can even help to advance system response and reduce requirements for repetitive adjustment by periodically "sampling" the ROI in the next mode that is likely (n+1 mode) while actively scanning the ROI in the current mode (n mode). Thus, interspersed with signal generation and acquisition for the current mode can be some amount of signal generation and acquisition for the anticipated next mode of imaging operation.

In a particular embodiment, the ultrasound system analyzes the entire displayed image for tissue and/or blood vessels during B-mode scanning. The system then identifies an ROI comprising particular tissue and/or blood vessels of interest. This ROI extent determination occurs in the background (i.e., is executed automatically by the ultrasound system) and preferably does not interrupt the progress of the examination being conducted by the sonographer. The ROI extent determination can be conditioned by prior knowledge of the exam type and can be accomplished by the system in transmitting, receiving and processing signals suited for a different, anticipated mode of operation that will be used next, with the system determining at which location the information of interest for the next mode resides. Information on the anticipated sequence of modes can be obtained according to the exam type or tissue preset, as described previously.

Once the ultrasound system determines the region of interest within the displayed ultrasound image, the system can generate a modified ultrasound image comprising the determined region of interest, wherein the modified ultrasound image is (in at least one embodiment) in color or in a representation different from the original, grayscale mode displayed image.

Alternatively, once the ultrasound system determines the region of interest within the displayed ultrasound image, the system can store or transmit the ROI extent information (e.g., geometric information or other representative of the ROI) such that a modified ultrasound image can be generated at a later time, wherein the modified ultrasound image shows the sample volume that includes the region of interest.

As an example of how this background processing can operate, consider a first ultrasound image acquired and displayed in B-mode. The system logic predicts that the second mode to be used is Color Flow. In anticipation of this switch to the second mode, a pulse sequence designed for Color Flow is sent out periodically while first mode imaging is being carried out. For example, signal emission and acquisition for the Color Flow mode can be interspersed with the B-mode image that is currently being displayed. The signals received in response to these pulses would be processed using known methods of Color Flow processing to determine spatial locations that exhibit flow. The algorithm can then automatically calculate a suitable ROI that would encompass the tissue and associated blood vessel(s) that were detected.

That is, the method will determine where the tissue and blood flow is, and perform the calculations needed to identify the volume coordinates most representative of the ROI extent. This information can be stored or transmitted, then used when the new imaging mode is activated. The ROI extent can be fully represented (e.g., by the geometric coordinates or shape such as by a square or rectangular or trapezoid box—as displayed on the ultrasound display).

Preferably, the determination of the ROI extent is automatic and computed in an ongoing manner. The continuous determination can be performed at predetermined time intervals selected by the system or according to operator configuration at set up. The determination is preferably conducted automatically, but may be manually assisted, such as by indication using outlining on a touch screen or other utility, for example.

The ROI extent information, as well as the modified ultrasound image itself can be stored (in either transient or non-transient form on either a local or remote server), so that it is readily accessible to the ultrasound system. Depending on the amount of storage that is available, ROI extent information for one or more regions of interest can optionally be stored and accessible. Also depending on the amount of storage made available, one or more modified ultrasound images can be optionally stored and accessible for viewing or transfer.

The steps of "determining a region of interest within the displayed ultrasound image" and "generating a modified ultrasound image" can be repeated as the sonographer continues the examination in the first viewing mode.

When the sonographer selects a second viewing mode, wherein the second viewing mode is different from the first viewing mode, then the ultrasound system switches to the second viewing mode with the ROI positioned as pre-calculated by this method. That is, the system displays the modified ultrasound image in response to the sonographer's selection of a second viewing mode, wherein the second viewing mode is different from the first viewing mode. In a preferred arrangement, the system displays a live version of the second viewing mode or the most-recent stored image.

With this method, the ROI being viewed in the first viewing mode is automatically positioned for viewing in the second viewing mode. That is, the sonographer does not need to reposition the ROI, thus saving the sonographer from extra key strokes or other instruction entries to return to the ROI of the earlier mode or to position the ROI in the sample volume of clinical interest.

Referring to FIG. 5, there is shown a modified ultrasound image that is displayed in response to the sonographer selection of a second viewing mode different from the first viewing mode as was shown in FIG. 4. The modified image includes the ROI from the image being displayed in the first viewing mode.

Figure 6:
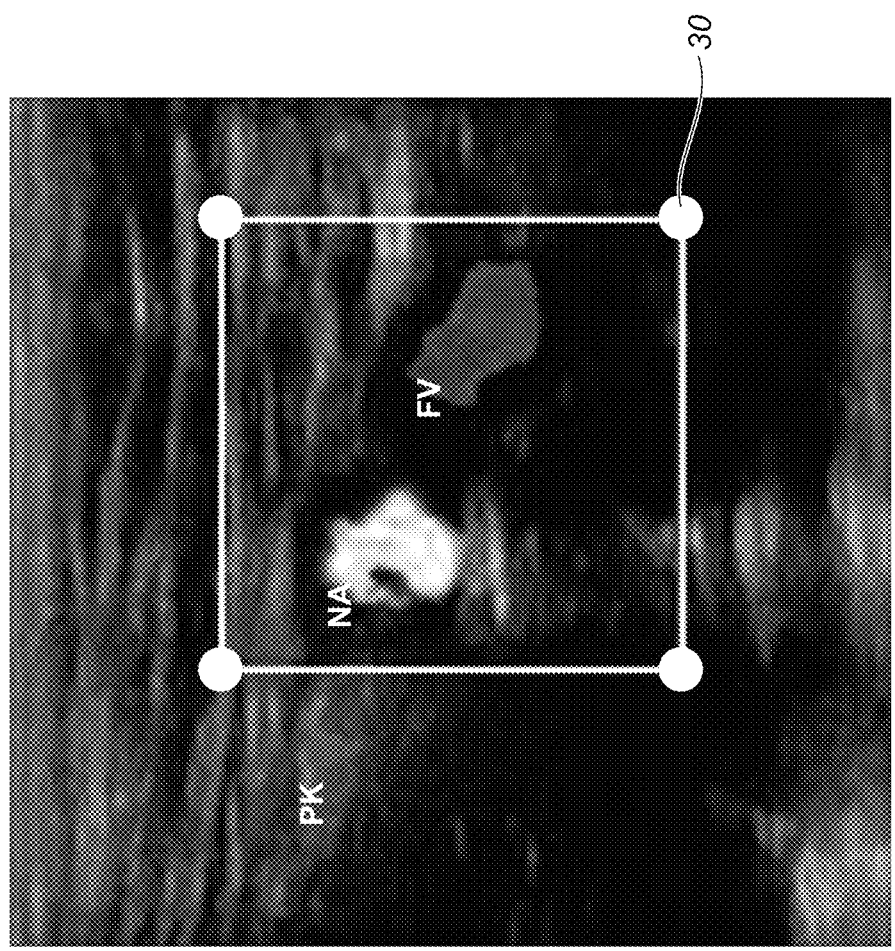
FIG. 6 shows a displayed ultrasound image having a region of interest, wherein a portion of the region of interest is highlighted in color.

FIGS. 5 and 6 both show a displayed ultrasound image having a region of interest, wherein a portion of the region of interest has a color, which illustrates particular types of tissue or fluids within a particular ROI.

This disclosure describes a method, comprising: (1) displaying, in response to a user selection of a first ultrasound viewing mode, an ultrasound image on a display, the ultrasound image being a grayscale image; (2) detecting at least one region of interest within the displayed image that comprises a tissue; (3) generating a modified ultrasound image comprising the at least one region of interest, the modified image rendered in color or having some other representation different from the displayed image; (4) repeating the steps of detecting and generating while in the first viewing mode; and (5) displaying, in response to the user selection, a second ultrasound viewing mode, wherein the generated modified image in the second viewing mode is different from that in the first viewing mode.

In at least one embodiment, ROI detection occurs automatically, with optional manual direction or instruction by the sonographer.

In at least one embodiment, the system automatically detects a tissue or other anatomy within the ROI. In at least one embodiment, the tissue is a blood vessel. In at least one embodiment, the system automatically detects a tissue characteristic within the ROI. In at least one embodiment, the tissue characteristic is a blood vessel.

In at least one embodiment, the step of repeating the detecting and generating steps are automatically accomplished without instruction or input by the sonographer.

According to another method, there is provided an ultrasound system having a display and a generator, wherein the system has a first and second operating and imaging mode, the first mode differing from the second mode. In response to a user selection of the first operating mode, the system displays an ultrasound image on the display, wherein the ultrasound image is grayscale. The ultrasound system detects at least one region of interest within the displayed image, and the ultrasound system detects a tissue within the detected region of interest. The ultrasound system generates a modified ultrasound image including the detected tissue, wherein the detected tissue is in color. The steps of detecting, detecting, and generating are repeated while in the first operating mode. In response to the user selection of the second operating mode, the modified image is displayed.

FIG. 6 illustrates another ultrasound image where a tissue has been detected within a region of interest. The illustrated tissue is a blood vessel and, in the example shown, the blood vessel appears highlighted, such as highlighted in color, while the remainder of the image is in grayscale. The ROI is defined by four points 30 that define a rectangle or other parallelogram.

Figure 7:
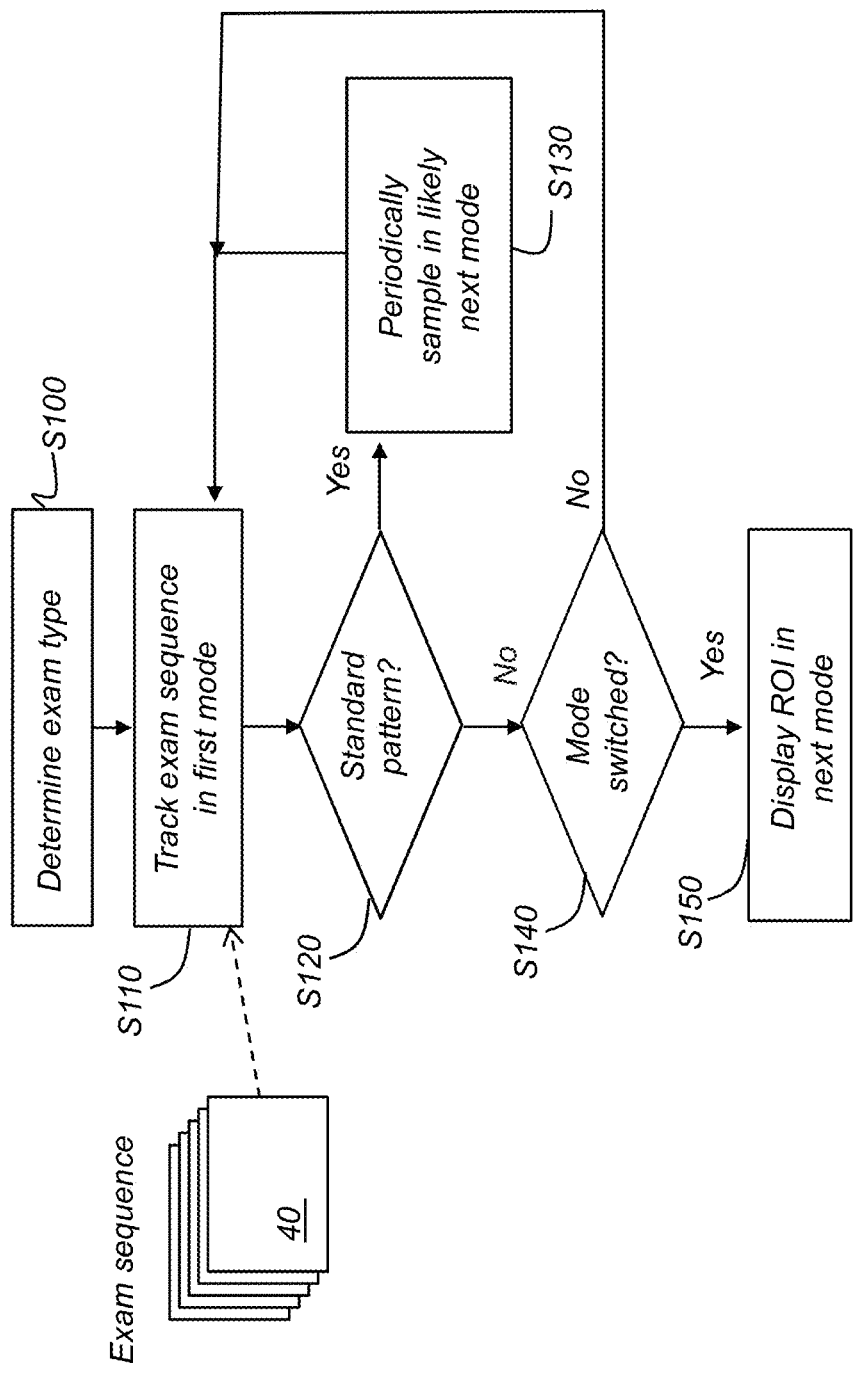
FIG. 7 is a logic flow diagram that shows a sequence of operation for ultrasound operation according to an embodiment of the present disclosure.

The logic flow diagram of FIG. 7 shows a sequence of operation for ultrasound operation according to an embodiment of the present disclosure. When the exam is initiated, processing determines the exam type in a determination step S100. This information can be from an operator entry, for example. As the exam progresses, the ultrasound system executes a standard tracking step S110, tracking exam steps and acquiring and displaying the ultrasound data in the first mode, typically B-mode as described previously. An optional set of stored exam sequences 40 can be used to provide data on likely mode changes for upcoming portions of the exam. Exam sequences 40 can be predetermined, stored and indexed based on standard steps used for particular exam types in general or at a specific site. An exam sequence 40 may use data for a previous exam for the patient. A pattern determination step S120 determines whether the exam being performed is following a stored sequence 40 pattern or is some other type of exam for which a sequence 40 has not been defined. If the sequence 40 can be determined, the system collects data on the likely ROI for the exam, based on data obtained from scanning in the initial mode. To determine the ROI, the system can use model anatomy data about the patient or about a larger patient population.

Continuing with the process flow of FIG. 7, a periodic scan step S130 is executed when the exam follows the pattern of a known exam sequence. During this step, ancillary processing is performed during unused processing cycles or the first mode sequence is momentarily interrupted at appropriate intervals, while the system executes one or two scan operations for setting up the next mode that is conventionally used in the sequence. This can include, for example, using the ROI determination performed by the system. In a mode checking step S140, the system responds to a mode change; until then, scanning in the first mode continues. When the mode change instruction is received from the operator, the system executes a display step S150, which changes the displayed data as scanning in the next mode begins. This scanning is informed by the pre-scanning information in step S130, allowing the system to identify the ROI, and to outline and highlight ROI areas on the display monitor.

Using the logic flow shown in FIG. 7, for example, the operator can first identify a general ROI using B-mode imaging, then switch to a color mode that observes blood flow. System logic can identify a portion of the ROI showing the blood flow and highlight that portion when the mode is switched. The displayed grayscale ultrasound image and the modified highlighted or otherwise enhanced ultrasound image can display simultaneously, such as in a non-overlapping arrangement.

Figure 8B:
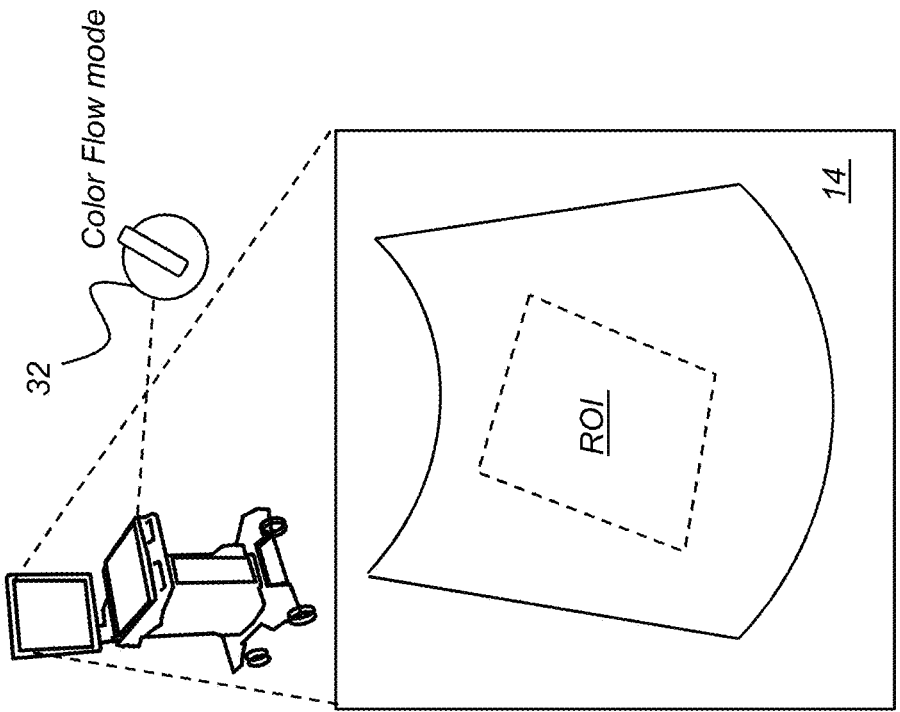
FIGS. 8A and 8B are schematic diagrams that show how the ultrasound system adapts to a standard mode change to provide the ROI needed by the viewer.
Figure 8A:
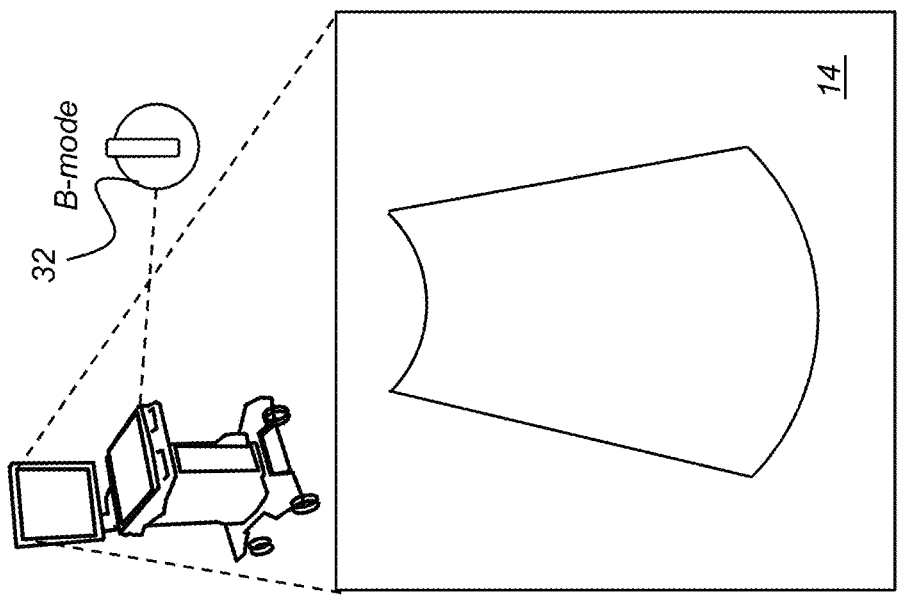

The schematic diagrams of FIGS. 8A and 8B show how the ultrasound system adapts to a standard mode change to provide the ROI needed by the viewer. In B-mode, as represented in FIG. 8A, the sonographer scans the patient anatomy in which the ROI is located. There is no specific indication of an ROI that is rendered in B-mode display. However, during B-mode scanning, the system, with or without sonographer assistance, can identify the ROI based on the exam type provided by the sonographer and based on information obtained from previous exams, for example. Then, when switched to Color Flow or other mode as shown using a switch 32 in FIG. 8B, the same ROI is presented appropriately for that mode.

Identification of a color box or other defining structure for the ROI in a second mode can be performed even when scanning is being executed in a first mode. For example, detection of a single heartbeat can inform the system where to locate the color box for the upcoming mode for a cardiac imaging exam.

This disclosure described an example using imaging in Color Flow mode as an embodiment. Those skilled in the art can recognize that a similar approach can be employed for other sequences of imaging mode selection. For example, an alternate sequence of modes can be used for elastography where the ROI is preferably positioned in the portion of the image having a maximum strain contrast.

The Applicant has described an automated colorbox placement method when switching from a grayscale imaging mode to a Color Flow or other ultrasound viewing mode.

The Applicant has described a method comprising: displaying, in response to a user selecting a first viewing mode, an ultrasound image on a display, the ultrasound image being in grayscale; determining a user's region of interest within the displayed ultrasound image; generating a modified ultrasound image comprising the region of interest, the modified ultrasound image being in color or in a representation different from the displayed image; and displaying, in response to a user selecting a second viewing mode, the modified ultrasound image, wherein the second viewing mode is different from the first viewing mode.

The Applicant has described a method comprising: displaying, in response to a user selection of a first viewing mode, an ultrasound image on a display, the ultrasound image being in grayscale; automatically determining a region of interest within the displayed ultrasound image, wherein the region of interest comprises tissue and/or a blood vessel; displaying, storing, or transmitting geometric information representative of the determined region of interest; generating a modified ultrasound image using the geometric information, the modified ultrasound image being in color or in a representation different from the displayed image; and displaying, on the display, the modified ultrasound image in response to a user selection of a second viewing mode different from the first viewing mode.

A preferred embodiment can be described as a software program. Those skilled in the art will recognize that the equivalent of such software may also be constructed in hardware. Because image manipulation algorithms and systems are well known, the present description will be directed in particular to algorithms and systems forming part of, or cooperating more directly with, the method in accordance with the present invention. Other aspects of such algorithms and systems, and hardware and/or software for producing and otherwise processing the image signals involved therewith, not specifically shown or described herein may be selected from such systems, algorithms, components and elements known in the art.

A computer program product may include one or more storage medium, for example; magnetic storage media such as magnetic disk (such as a floppy disk) or magnetic tape; optical storage media such as optical disk, optical tape, or machine readable bar code; solid-state electronic storage devices such as random access memory (RAM), or read-only memory (ROM); or any other physical device or media employed to store a computer program having instructions for controlling one or more computers to practice the method according to the present invention.

The methods described above may be described with reference to a flowchart. Describing the methods by reference to a flowchart enables one skilled in the art to develop such programs, firmware, or hardware, including such instructions to carry out the methods on suitable computers, executing the instructions from computer-readable media. Similarly, the methods performed by the service computer programs, firmware, or hardware are also composed of computer-executable instructions.

The invention has been described in detail with particular reference to a presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

What is claimed is:

1. A method, comprising:
providing an ultrasound system having a display and a generator, the ultrasound system having a first operating mode and a second operating mode, the first operating mode differing from the second operating mode;
the ultrasound system displaying, in response to a user selection of the first operating mode, only a monochromatic ultrasound image on the display entirely in grayscale;
the ultrasound system detecting a region of interest within the displayed monochromatic ultrasound image during the step of displaying only the monochromatic ultrasound image entirely in grayscale;
the ultrasound system detecting a tissue within the detected region of interest during the step of displaying only the monochromatic ultrasound image entirely in grayscale;
the ultrasound system generating a polychromatic ultrasound image including the detected tissue during the step of displaying only the monochromatic ultrasound image entirely in grayscale, the generated polychromatic ultrasound image including the detected tissue highlighted in color or in a representation different from the displayed monochromatic ultrasound image;
the ultrasound system repeating the steps of detecting a region of interest, detecting the tissue within the detected region of interest, and generating the polychromatic ultrasound image while displaying only the monochromatic ultrasound image entirely in grayscale in the first operating mode; and
the ultrasound system displaying, in response to a user selection of the second operating mode, the generated polychromatic ultrasound image including the detected tissue.

2. The method of claim 1, wherein the step of the ultrasound system detecting the region of interest comprises accepting an operator command associated with detecting the region of interest.

3. The method of claim 1, further comprising detecting a blood vessel within the detected region of interest.

4. The method of claim 1, wherein at least one of the steps of the ultrasound system detecting the region of interest and the ultrasound system generating the polychromatic ultrasound image is repeated automatically during the step of the ultrasound system displaying only the monochromatic ultrasound image entirely in grayscale.

* * * * *